(12) United States Patent
Klapper et al.

(10) Patent No.: US 11,951,306 B2
(45) Date of Patent: *Apr. 9, 2024

(54) ELECTRICAL SYSTEM COMPRISING A PLURALITY OF ELECTRIC CIRCUITS AND ANTI-CURRENT PROTECTION EQUIPMENT

(71) Applicant: Adaptive Regelsysteme Gesellschaft M.B.H., Salzburg (AT)

(72) Inventors: Ulrich Klapper, Rankweil (AT); Wernich de Villiers, Dornbirn (AT)

(73) Assignee: Adaptive Regelsysteme Gesellschaft M.B.H., Salzburg (AT)

( * ) Notice: Subject to any disclaimer, the term of this patent is extended or adjusted under 35 U.S.C. 154(b) by 652 days.

This patent is subject to a terminal disclaimer.

(21) Appl. No.: 17/254,593

(22) PCT Filed: Jun. 19, 2019

(86) PCT No.: PCT/EP2019/066118
§ 371 (c)(1),
(2) Date: Dec. 21, 2020

(87) PCT Pub. No.: WO2019/243381
PCT Pub. Date: Dec. 26, 2019

(65) Prior Publication Data
US 2021/0128909 A1 May 6, 2021

(30) Foreign Application Priority Data
Jun. 21, 2018 (AT) .............................. A 50513/2018

(51) Int. Cl.
*A61N 1/16* (2006.01)
*A61B 5/00* (2006.01)
(Continued)

(52) U.S. Cl.
CPC ................. *A61N 1/16* (2013.01); *A61B 5/05* (2013.01); *A61B 5/6804* (2013.01);
(Continued)

(58) Field of Classification Search
CPC ........ H02H 5/12; H02H 1/0007; H02H 3/033; H02H 3/044; H02H 3/16; A41D 1/002;
(Continued)

(56) References Cited

U.S. PATENT DOCUMENTS 3,784,842 A    1/1974   Kremer
4,310,770 A *   1/1982   Keener ..................... H02J 3/14
                                                  307/35
(Continued)

FOREIGN PATENT DOCUMENTS

DE    3903025 A1   8/1990
DE    4438063 A1   5/1995
(Continued)

*Primary Examiner* — Elim Ortiz
(74) *Attorney, Agent, or Firm* — Dykema Gossett PLLC (57) ABSTRACT

Aspects of the present disclosure are directed to increasing protection against electric shocks when a person is working on an electrical system. In some embodiments, the electrical system includes at least two different circuits and a safety module. An emergency signal input is provided on the safety module, and when an external emergency signal is received via the emergency signal input, the safety module shuts off a configured first circuit the associated switch and at least one further circuit via the associated switch if the safety module still receives the emergency signal at the emergency signal input after a predetermined period of time.

24 Claims, 4 Drawing Sheets

(51) Int. Cl.
  *A61B 5/05*    (2021.01)
  *H02H 1/00*    (2006.01)
  *H02H 5/12*    (2006.01)
  *G05B 9/02*    (2006.01)

(52) U.S. Cl.
  CPC ............ *H02H 1/0007* (2013.01); *H02H 5/12* (2013.01); *G05B 9/02* (2013.01)

(58) Field of Classification Search
  CPC ...... A41D 13/008; A41D 1/005; A41D 31/26; A61N 1/16; A61B 5/05; A61B 5/6804; G05B 9/02; G01R 19/15; G08B 21/02
  See application file for complete search history.

(56) References Cited

U.S. PATENT DOCUMENTS 5,844,326 A * 12/1998 Proctor ..................... H02J 3/14
                                                    361/93.7
2019/0319449 A1    10/2019 Gegenbauer et al.

FOREIGN PATENT DOCUMENTS

EP        4184180 A1 *  5/2023  ........... G01R 19/145
WO     2018114304 A1     6/2018

\* cited by examiner

ELECTRICAL SYSTEM COMPRISING A PLURALITY OF ELECTRIC CIRCUITS AND ANTI-CURRENT PROTECTION EQUIPMENT

CROSS-REFERENCE TO RELATED APPLICATIONS

This application is a national stage filing based upon International PCT Application No. PCT/EP2019/066118, filed 19 Jun. 2019, which claims the benefit of priority to Austria application No. A 50513/2018, filed 21 Jun. 2018.

BACKGROUND

The present invention relates to an electrical system with a plurality of electrical circuits, each with a switch for switching off the associated circuit, a system for performing work on the electrical system and a method to perform work on the electrical system by a person.

It is common in electrical systems, especially in an industrial environment, to provide an emergency stop in order to switch off a conducting or live component that is part of the emergency stop circuit if a person touches the same. With such safety devices, the protection against electric shock due to an unintentional contact of people working on conducting parts or live parts can be increased by other people present triggering the emergency stop in the event of a fault. However, this requires that at least one further person is in the vicinity of an electrical accident and has knowledge of the electrical accident, which is not always the case.

Normally, however, a number of different circuits are implemented in electrical systems. Switching off an emergency stop circuit cannot therefore ensure that the component that is touched is actually switched off after the emergency stop has been activated. There is therefore a certain residual risk for persons working in the vicinity of the electrical system. Other common safety devices in electrical systems are circuit breakers for switching off circuits in the event of an unacceptable electrical current and ground-fault circuit interrupters that are intended to respond in the event of unacceptable earth fault currents. However, these can only provide protection if they actually trip in the event of an error. Due to possible high operating currents or slow reaction times, there may be a danger for people working on the electrical system despite such safety devices.

Methods and devices for a better protection of persons against unacceptable electrical body currents are already known. DE 39 03 025 A1, for example, describes such a method and such a device, wherein an electrode connected to a control device is arranged on at least two extremities of the person, for example on the arms or legs. Via the electrodes, the control device detects a body current caused by a contact with an external electrical potential. If such a current flow is detected, the control device activates a shutdown device with which the further supply of current to the contact point is interrupted. The electrodes and the control device can be arranged on an item of clothing with a wireless connection between the control device and the switch-off device. DE 44 38 063 A1 describes a similar protective device.

Such protective devices can increase the safety of persons working on conducting parts or live parts against electric shock due to unintentional contact.

It is therefore the object of the present invention to increase the protection against electric shocks when a person is working on an electrical system with at least two different electric circuits.

SUMMARY OF THE INVENTION

According to the invention, this object is achieved in that a safety module is provided on the electrical system, with an emergency signal input being provided on the safety module, and in that, when an external emergency signal is received at the emergency signal input, this input switches off a configured first circuit via the associated switch and at least one further circuit via the associated switch if the safety module still receives the emergency signal at the emergency signal input after a specified period of time. This means that an electric circuit can be switched off when an emergency signal is received, with a plurality of circuits being switched off if the emergency signal is still present despite an initial switching action. This can increase the safety of the person who works on the electrical system. Any number of switching operation hierarchies can be defined as well.

The emergency signal is particularly advantageously generated with a protective device for detecting an electrical body current and worn by the person, and which device outputs and transmits an emergency signal to the emergency signal input of the safety module. As soon as the protective device detects an unacceptable body current (which can be configured accordingly), an emergency signal is triggered, which then triggers the switching action by the safety module. In this way, the protection of the person is no longer tied to the presence of another person, who forces a switching action, for example, by pressing an emergency stop.

Further advantageous embodiments and effects of the invention can be gathered from the dependent claims and the following description.

BRIEF DESCRIPTION OF THE DRAWINGS

In the following, the present invention is described in greater detail with reference to FIGS. 1 to 8, which, by way of example, show schematic and non-limiting advantageous embodiments of the invention. In the drawings.

DETAILED DESCRIPTION

Work on an existing electrical systems 10, for example on a control cabinet or an electrical distributor, or also on connected consumers 53 located in the electrical system 10, often has to be carried out by a person 8. In such an electrical system 10, a plurality of electrical circuits 51 are usually provided, wherein the present invention assumes at least two electrical circuits 51a, 51b, but any number of electrical circuits can likewise be present. Such an electrical system 10 is shown as an example in FIG. 1. Electrical systems 10 generally include switches 54a, 54b (automatic circuit breakers) for the circuits 51a, 51b in order to switch an electric circuit 51a, 51b to a voltage-free state. Any electrical consumer 53a, 53b can be provided in an electric circuit 51a, 51b. A typical example of the electrical system 10 is an electrical distributor of a building with a plurality of automatic circuit breakers and safety switches (ground-fault circuit interrupter or total current circuit breaker) as switch 54. Another example is a control cabinet for a production plant. In order to carry out work on electrical circuits 51a, 51b, these circuits are usually switched to a voltage-free state, for example by the associated switches 54a, 54b, such as automatic circuit breakers, for example. However, it is also possible that certain circuits 51a, 51b may not be disconnected from the power supply, which means that work on this electrical circuit 51a, 51b must be carried out under voltage. This can be the case, for example, in a production or manufacturing plant or in machine tools, where switching off an electrical circuit 51a, 51b can lead to an undesired interruption of operation. Often, sockets 52a, 52b are also provided in the circuit 51a, 51b, to which electrical consumers can be connected as well.

Furthermore, especially in an industrial environment, it is conceivable that an electric circuit 51a is designed as an emergency stop circuit. For this purpose, at least one well-known emergency stop switch 20 is integrated in this circuit 51a, which, when actuated, disconnects the electric circuit 51a from voltage, for example via a disconnection unit 23, such as a disconnection relay, as shown in FIG. 1.

A safety module 22 with an emergency signal input 21 is provided in order to protect a person 8 working on such an electrical system 10 with at least two electric circuits 51a, 51b or consumers 53a, 53b from electric shocks. The safety module 22 can be arranged, for example, in the control cabinet or in the distributor but can also be arranged in the region of the circuit 51a, 51b or a consumer 53a, 53b.

Figure 1:
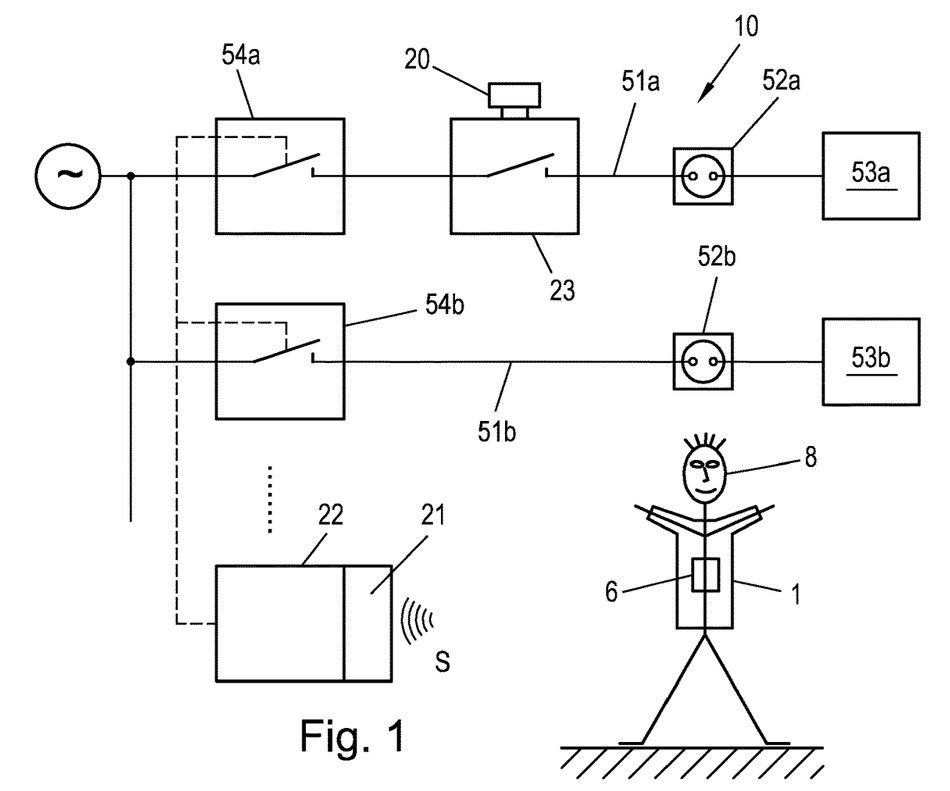
FIG. 1 shows an inventive electrical system.

An external emergency signal S can be received at the emergency signal input 21, for example in a wired or wireless manner (as seen in FIG. 1). If the emergency signal input 21 receives an emergency signal S, the safety module 22 triggers a switching action which shuts off the voltage in an electric circuit 51a, 5ab. For this purpose, the safety module 22 can open a switch 54a, 54b of a circuit 51, 51b, either directly or indirectly. A direct opening could for example be realized by a switch 54a, 54b with an external switching input. For an indirect opening, the circuit 51a, 51b could be short-circuited (for example by connecting a phase to the neutral conductor), which would trigger the automatic circuit breakers (as switches 54a, 54b). The safety module 22 could also generate a sufficient earth fault current in the electrical circuit 51a, 51b, for example, by connecting a phase to the ground via a resistor, which would trigger a ground-fault circuit interrupter (as switch 54a, 54b). The safety module 22 could also act on any emergency stop switch 20 (as switches 54a, 54b) in order to actuate the disconnection unit 23 so that the disconnection unit 23 interrupts the circuit 51a, 51b. Which type of action is triggered naturally depends on the type and design of the electrical system 10 and can be adapted accordingly.

The external emergency signal S is generated in order to protect the person 8 working on the electrical system 10 from an electrical accident or from the effects of an electrical accident. When working on live parts, it is possible for the person 8 to touch a live part of the electrical system 10, which can lead to an electric shock from an electric current that flows through the body of the person 8. The triggering of the safety module 22 via the externally received emergency signal S is intended to switch off the circuit 51a, 51b on which the person 8 is working in order to minimize the duration of an electric shock.

Situations are conceivable in which a switching operation is carried out on the electrical system 10 by the emergency signal S, but this does not lead to the desired success, i.e., the absence of voltage on the part contacted. This can happen, for example, if an emergency circuit is interrupted but another circuit remains under voltage. It is therefore provided that the safety module 22 monitors whether the switching action leads to the desired success within a predetermined period of time, for example 100 ms, namely a determination that the emergency signal S is no longer being received by the protective device 1. This is to be equated with the successful voltage shut-off in the circuit 51a, 51b or with the loss of contact between the person 8 and the component of the electrical system 10 that is under voltage. If it is not possible to determine during the specified period of time that there is no voltage, the safety module 22 triggers a further switching operation in the electrical system 10. For this purpose, a hierarchy of the electric circuits 51a, 51b can be defined in the safety module 22, which circuits are switched off, one after the other, as long as an emergency signal S is received.

It can be provided that a plurality of circuits 51a, 51b are switched off at the same time in a hierarchical level, either by opening all switches 54a, 54b of the affected electric circuits 51a, 51b or by implementing a corresponding switching hierarchy.

Figure 2:
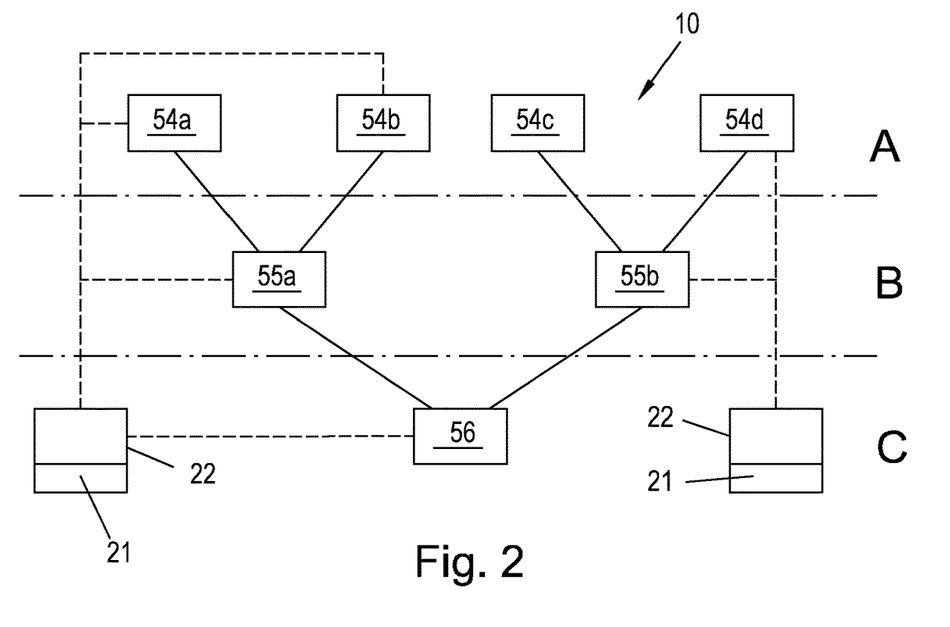
FIG. 2 shows a a switching operation hierarchy in the electrical system.

This hierarchy can, for example, be defined in a tree-like manner with several hierarchy levels A, B, C, as shown in FIG. 2. The switches 54a, 54b (etc.) that are first switched by the safety module 22 are provided in the first hierarchy level A. These are, for example, the switches 54a, 54b for the individual electric circuits 51a, 51b. If a switching action in this hierarchy level A is unsuccessful, then another circuit in this hierarchy level A can be switched off as the next switching action, whereby the order, for example adjacent circuits first and then others, can likewise be defined. If this is also unsuccessful, then a switch 55a of the next hierarchy level B can be actuated, which switches off all downstream electric circuits 51a, 51b. Alternatively, all switches 54a, 54b of the downstream electric circuits 51a, 51b can also be activated for opening. In this way, for example, all electric circuits of a part of a building, for example an entire floor, could be switched off. In a next hierarchy level C, all electric circuits of a building could then be switched off. It is obvious that the hierarchies can be freely configured. In the same way, the order in which the circuits 51a, 51b are deactivated can be freely configured as well.

A plurality of safety modules 22 could also be provided in the electrical system 10, as indicated in FIG. 2, with each safety module 22 being responsible for different parts of the electrical system 10.

In order to generate an emergency signal S in the event of an electric shock, the person 8 can additionally be equipped with a protective device 1 against electric shock, as indicated in FIG. 1. Such a protective device and its basic function are generally known from prior art. DE 39 03 025 A1, for example, describes such a method and such a protective device, wherein an electrode connected to a control device is arranged on at least two extremities of the person, for example on the arms or legs. The control device detects a body current via the electrodes caused by a contact with an external electrical potential. If such a current flow is detected, the control device activates a shutdown device with which the further supply of current to the contact point is interrupted. The electrodes and the control device can be arranged on an item of clothing with a wireless connection between the control device and the switch-off device. DE 44 38 063 A1 describes a similar protective device.

Figure 3:
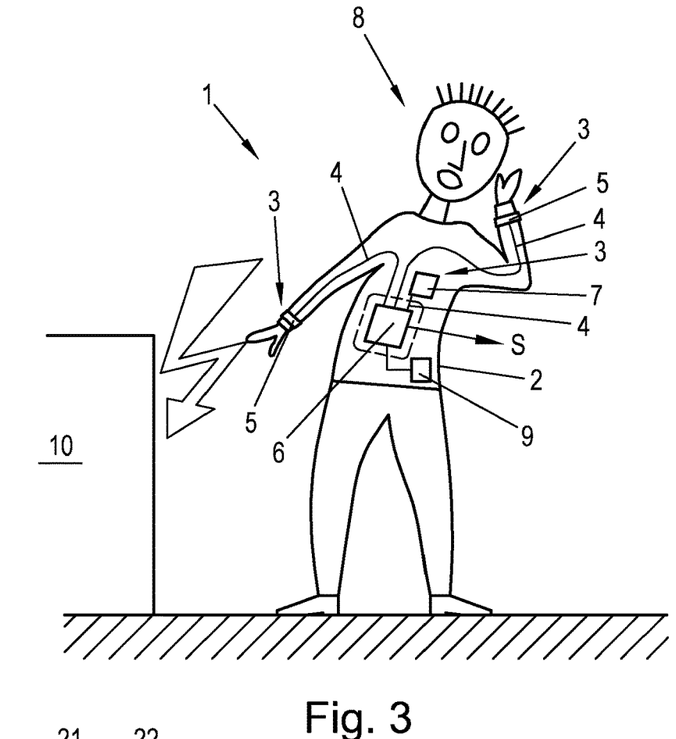
FIG. 3 shows a protective device worn by a person.

The present invention uses a protective device 1, the basic function of which is known from prior art and which is explained in more detail with reference to FIG. 3 for a better understanding. The protective device 1, or at least parts thereof, is arranged on or integrated in an item of clothing 2, in this case a shirt. Of course, other items of clothing 2, for example trousers, a sweater, a T-shirt, a jacket, overalls, etc., can also be used. Even combinations of several items of clothing 2 are also possible, for example a combination of trousers and shirt, etc. At least one sensor 3 is arranged on the item of clothing 2 in order to detect an electrical body current flowing through the human body. Electrodes 5 can, for example, be used as a sensor 3 in order to detect an electrical potential or an electrical current. The electrodes 5 are preferably arranged at exposed locations on the item of clothing 2, for example in the region of the extremities, i.e., for example on sleeves, trouser legs or hoods. A biometric sensor 7 can also be used as a sensor 3 in order to detect a biometric signal, for example the heart rate, the amplitude or the course of the heartbeat, the respiratory rate, the skin resistance, etc. By evaluating the biometric signal, in particular the heartbeat (frequency, amplitude and/or course), conclusions can also be drawn about a flowing electrical body current.

For this purpose, the sensor 3, or the sensors, can preferably be integrated in the item of clothing 2 but can also be applied separately, for example by means of a cuff, bracelet or belt. In a possible embodiment, a sensor 3 could be designed as an electrode 5 in the form of a known Rogowski coil (as in FIG. 3) in order to detect an electrical current flowing through an extremity or another part of the human body. For this purpose, the electrode 5 can be placed in a ring around an extremity, for example in a waistband of a sleeve or a trouser leg of the item of clothing 2. In order to detect an electrical potential, the electrode 5 must be in contact with the skin in an electrically conductive manner, whereas this would not be absolutely necessary in the case of a Rogowski coil, for example. A resistance measurement can also be carried out regularly or continuously between two electrodes 5 in order to check whether the item of clothing 2 is properly connected to the body of the person 8. In order to detect the heartbeat, a corresponding biometric sensor 7, for example a heart rate sensor, could be integrated in the item of clothing 2 in the region of the chest, or a corresponding chest strap could be applied.

A sensor 3 is connected via at least one signal line 4 to an evaluation unit 6 (for example, in the form of a computing unit, possibly also with corresponding software). The signals detected by the at least one sensor 3 are evaluated in the evaluation unit 6. An electrical potential detected with an electrode 5 as the sensor 3 or a detected flowing electric current can be evaluated, for example. An applied electrical voltage can be determined between two detected electrical potentials, for example with two sensors 3 designed as electrodes 5, and evaluated in the evaluation unit 6. A resistance measurement can also be carried out regularly or continuously between two electrodes 5 in order to check whether the item of clothing 2 is properly connected to the body of the person 8. The evaluation of the body current or of a potential difference can likewise be carried out with suitable hardware or digitally, which requires an A/D conversion and the corresponding hardware and software. In the event that a dangerous body current is detected, for example when an abnormal heartbeat, a dangerous current flow or a dangerous potential difference (voltage) between two electrodes 5 is detected, which in turn indicates a current flow through the body, the evaluation unit 6 generates an emergency signal S which can be used to trigger a desired action. For this purpose, corresponding limit values for an acceptable body current, for example an acceptable potential difference or an acceptable current, can of course also be stored or specified in the evaluation unit 6, which can also be adjustable. Likewise, patterns of a biometric signal that indicate a dangerous body current can also be stored in the evaluation unit 6.

Advantageously, different sensors 3 can be provided on the item of clothing 2 in order to increase the reliability of the detection of dangerous electrical body currents. For example, electrodes 5 could be provided on extremities and additionally a biometric sensor 7 for detecting the heartbeat, as shown in FIG. 3.

The safety of the protective device 1 can also be increased by providing redundancies. For example, more than one signal line 4 can be provided per sensor 3 so that possible cable breaks or contact errors do not have to lead to a failure of the safety function, or a cable break or contact error can even be recognized and possibly also indicated.

The evaluation unit 6 is preferably held or carried by the person 8 who wears the protective device 1. This evaluation unit could be arranged, for example, in a shoulder bag or a backpack, but could also be pouched into a pocket of the item of clothing 2 or could also advantageously be integrated, wholly or partially, in the item of clothing 2, for example in the form of an intelligent item of clothing with integrated electronics.

The emergency signal S can in principle be emitted in a wired or wireless manner and can be received at the emergency signal input 21 in a wired or wireless manner.

The protective device 1 thus consists, for example, of an item of clothing 2 with at least one sensor 3 and an evaluation unit 6 which is connected to the at least one sensor 3 by at least one signal line 4 and which evaluates a signal detected by the sensor 3 in order to detect a dangerous electrical body current. The emergency signal S of the evaluation unit 6, or generally of the protective device 1, can be used by the safety module 22 to trigger certain configured actions in order to increase the protection of a person 8 against electric shock.

In the protective device 1, preferably on the item of clothing 2 or on an external unit that is in data connection with the protective device 1, at least one further sensor 9 can optionally be provided for detecting a further variable (FIG. 1), which detects a further condition of the person 8 (in addition to a possible body current). The further sensor 9 can, for example, be an acceleration sensor in order to be able to determine a fall of the person 8. A position sensor as a further sensor 9 can be used to detect if the person 8 is lying down. The further sensor 9 can be designed to record an ECG (electrocardiogram) which, in connection with an electrical accident, can provide important information about the condition of the person 8 having the accident. The respiration of the person victim 8 having the accident can also be recorded by means of an acceleration sensor or movement sensor as a further sensor 9. Of course, several further sensors 9 can also be provided on the protective device 1 with any combinations of the above sensors 9 being conceivable.

Values acquired with the sensor 3, or the sensors 3, and/or values acquired with at least one further sensor 9 can also be stored in the protective device 1 in a memory unit, for example in evaluation unit 6. This makes it possible to read stored values at a later point in time or to transmit them to other locations.

If the protective device 1 detects a contact between the person 8 and a conducting or live part of an electrical system 10 as described above, which causes an unacceptable body current to flow through the person 8, an emergency signal S is triggered, for example wirelessly, such as via a radio link. The protective device 1 thus triggers a configured switching operation via the emergency signal input 21 of the security module 22 on the electrical system 10, which is aimed at switching off at least the part that a person 8 is touching. When the protective device 1 is activated, however, an electric shock has already occurred in these situations. The affected person 8 can, however, sometimes work in very remote places or alone, so that despite the activation of the protective device 1, there is no help for the person 8 having the accident. The same applies if the protective device 1 fails for whatever reasons, i.e., the protective device 1 responds, but the voltage cannot be switched off.

Figure 4:
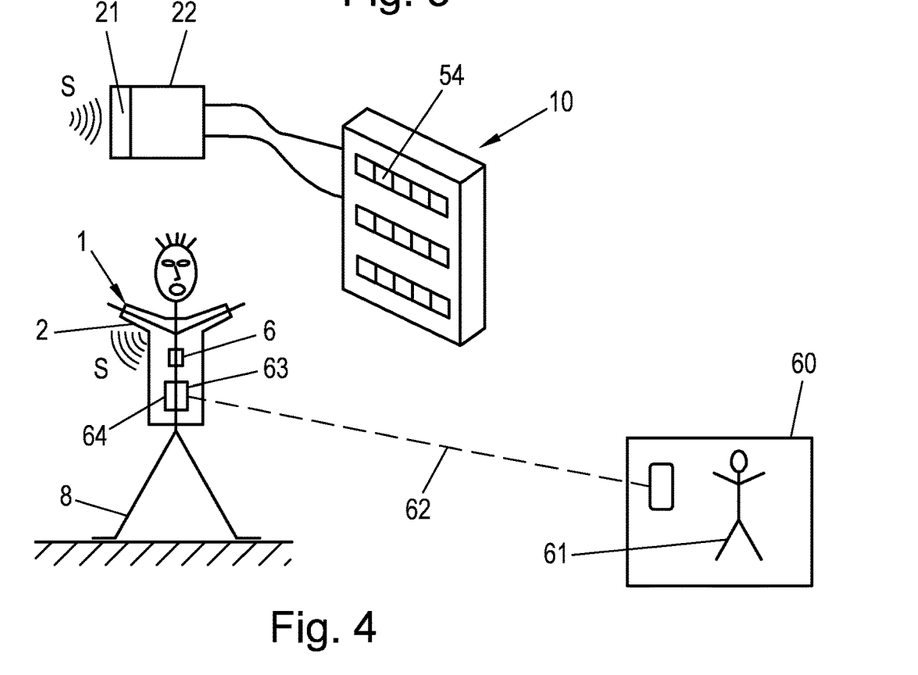
FIG. 4 shows an exemplary embodiment of the method according to the invention for notifying a remote location of an electrical accident involving a person wearing a protective device.

It can likewise be provided that a protective device 1 does not only generate an emergency signal S but establishes a radio link 62 (indicated by the dashed line) with a transmitter unit 64, such as a mobile radio transmitter 63, to a configured remote location 60 so that help for the person 8 having the accident is initiated or coordinated, preferably by a further person 61 at the remote location 60, as shown in FIG. 4. "Remote" means in this context that this further person 61 is at least so far away from the person 8 having the accident that this further person 61 can neither visually nor acoustically directly determine the condition of the accident victim. The further person 61 can, for example, be in an emergency center, which can be in a completely different location. The protective device 1 can establish the radio link 62 directly via the transmitter unit 64, for example by means of a mobile radio transmitter 63 which is integrated in the item of clothing 2, for example again as part of intelligent clothing.

Figure 5:
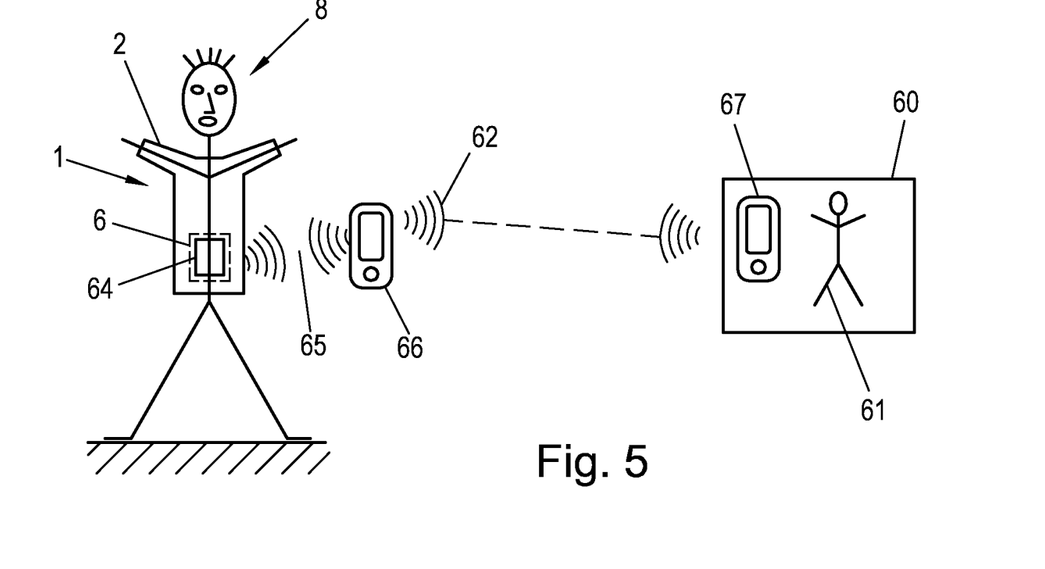
FIG. 5 shows the use of a mobile terminal for establishing the radio link to the remote location.

Alternatively, the protective device 1 can also establish the radio link 62 indirectly, for example, in that the protective device 1 connects, via the transmitter unit 64 and a suitable data connection 65, for example Bluetooth, to a mobile terminal 66, for example a smartphone (e.g., using Bluetooth), of the person 8, which then sets up the radio link 62 to the remote location 60, as shown in FIG. 5. A specific message can be sent via the radio link 62, for example a text message (SMS), a data transmission (for example, by e-mail) or a call can be made. The further person 61 in the remote location 60 can also carry a mobile terminal 67 with him, which can be connected to the radio link 62 if necessary, for example via a mobile radio network. It is obvious that the remote location 60 (e.g., the emergency center) does not have to be stationary, in particular, if the further person 61 also uses a mobile terminal 67 to be contacted.

The transmitting unit 64, for example in the form of a mobile radio transmitter 63, is preferably integrated in the evaluation unit 6 or also in the item of clothing 2 itself (for example, in the form of intelligent clothing). The transmitting unit 64 can be controlled by the evaluation unit 6 of the protective device 1.

The further person 61 can then coordinate help for the person 8 having the accident. An emergency center may, for example, be aware of the location of persons 8 who work on electrical systems 10 that are live or under voltage. For example, maintenance work is planned on an electrical system 10 (as in FIG. 4), and it is known when and where this will be carried out. The protective device 1 can be assigned to a specific person 8 and can also have a unique identifier (for example, a mobile phone number). This way, an emergency call (also as a text message or an e-mail) coming into the emergency center from a protective device 1 can be assigned to a location and/or a person 8 so that the further person 61 can be specifically coordinated help by an emergency helper.

The protective device 1 can also be equipped with a positioning unit 72. For this purpose, for example, the positioning unit 72 such as a GPS (Global Positioning System) sensor can be arranged on the item of clothing 2 (as indicated by dashed lines in FIG. 6) or integrated in the item of clothing, for example intelligent clothing with integrated electronics. Other satellite navigation systems such as GALILEO can also be used, of course. However, there are naturally other ways of determining the position of a person 8 by means of a positioning unit 72. A conclusion about the current position could be drawn, for example, from the availability of WLAN (Wireless LAN) networks. A position could also be determined via a mobile radio network, for example, by means of GSM positioning.

Figure 6:
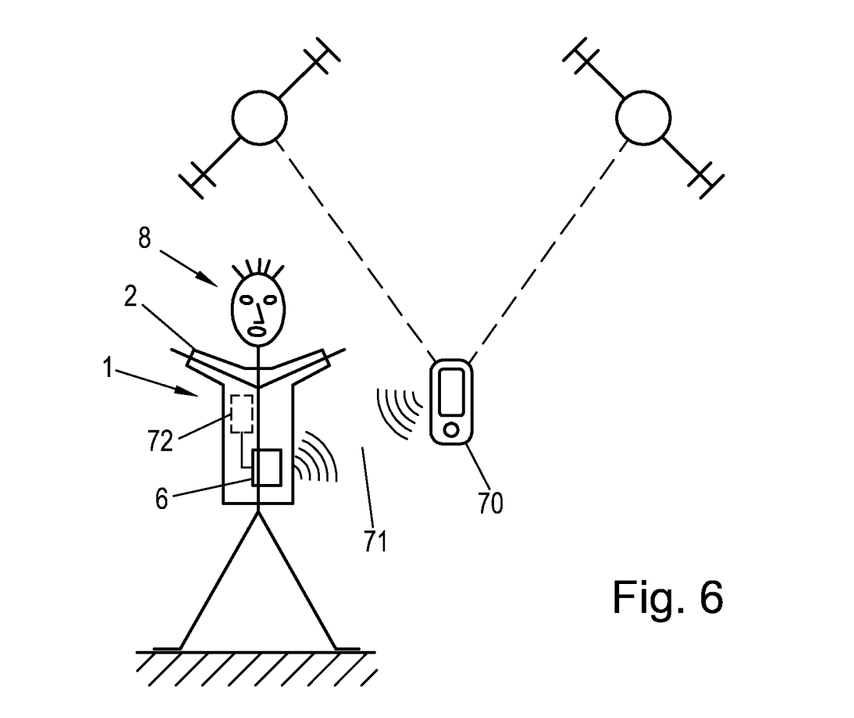
FIG. 6 shows the additional detection of the position of the person.
Figure 7:
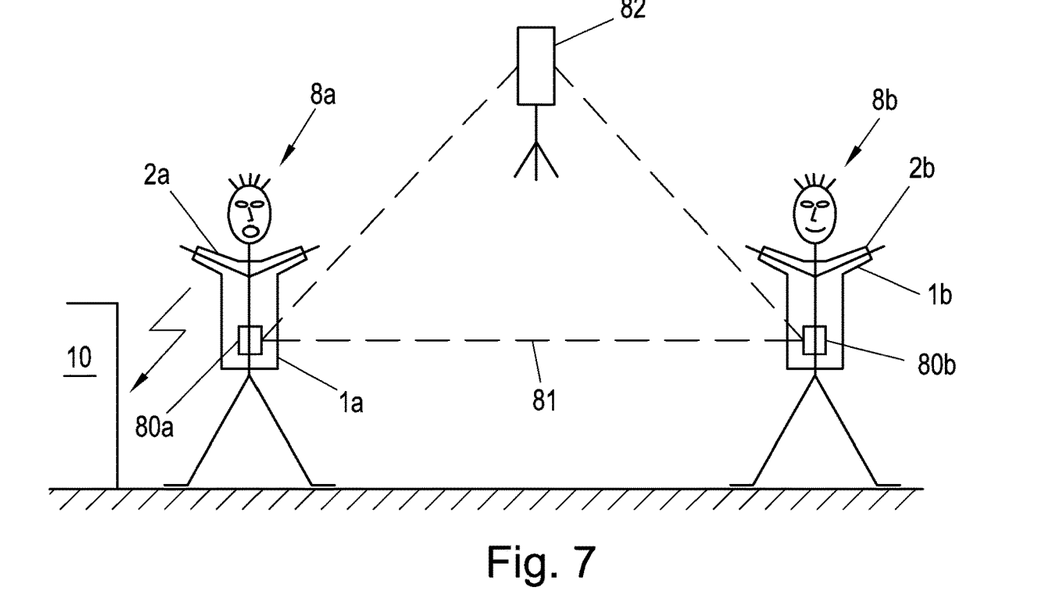
FIG. 7 shows a possible communication link between two protective devices and FIG. 8 shows a system with a plurality of radio receivers for transmitting the emergency signal from the protective device to an electrical system.

The protective device 1 can, however, also be connected to an external unit 71, which can carry out a position determination, as a positioning unit 72, as shown, for example, in FIG. 7. Today's mobile telephones or smart phones generally have a positioning system integrated in them so that a mobile terminal 66 can be used particularly advantageously as an external unit 71 for this purpose (as seen in FIG. 6). However, the external unit 71 can be a GPS receiver as well. The protective device 1 can thus be connected to the external unit 71 via a suitable data link 65, for example Bluetooth, in order to receive the current position of the person 8 from the external unit 71. To establish the link, a transmitting unit 64 could again be provided in the protective device 1, for example.

The current position can be stored in the protective device 1, preferably in the evaluation unit 6 of the protective device 1, preferably with further details about an electrical accident such as the date, time, duration of the body current or the level of the current flow, in order to allow for a later evaluation. The current position is understood to refer both to geographic coordinates and a specific location. Since many external units 71 often also have a positioning function, the location can also be used directly as the current position.

Of course, the current position or the current location can also be transmitted to the remote location 60 (as in FIG. 4 or 5) in order to assist with the coordination of assistance for the person 8 having the accident. The current position or the current location could also be transmitted to the remote location 60 at certain time intervals in order to always know a current position or a current location of the person 8.

Independently of the other functions of the protective device, the position or the location of the person 8 can be recorded and stored in the protective device 1, for example in order to generate a documentation of electrical accidents or for statistical records or evaluations of electrical accidents. In addition, further details such as date, time, duration of power contact, etc. can be stored.

It is obvious that when a remote location 60 is notified by the protective device 1 in the event of an electrical accident, additional information, for example data from further sensors 9 on the protective device 1, can also be transmitted about the condition of the person 8, for example the physical position of the person 8 (fall, person is lying down), pulse, ECG, respiration. Such additional information can be important for coordinating the help and rescue operations.

The remote location 60 can, of course, also be automated to the extent that, in the event of an incoming message of an electrical accident of a person 8, certain actions are automatically taken, for example the notification of an ambulance service or helper, possibly also with the specific position or location of person 8, possibly also with other existing data. In this case, the further person 61 would not be absolutely necessary.

To this end, the remote location 60 could also determine the location of one or more helper in the vicinity of the person 8 having the accident and specifically inform him about the electrical accident. The helper who is locally closest to the person 8 having the accident is preferably determined. For this purpose, the helper can be equipped with a communication unit, for example a mobile phone or smart phone, which is contacted by the remote location 60 or by the further person 61 at the remote location 60 with a corresponding message. The message could be a text message, email, or the like, or a phone call.

A helper in the vicinity of the person having the accident could be determined in that the locations of all possible helpers are known at the remote location 60. The current location could be continuously transmitted to the remote location 60, for example, via the communication units of the EMT helpers at predetermined intervals. However, a proximity could also be determined in such a way that it is determined whether a communication unit of the person 8 having the accident, for example a mobile terminal 66, can exchange messages with a communication unit of a helper, for example via Bluetooth, or whether both can receive the same WLAN network. This could also be continuously communicated to the remote location 60 by the respective communication unit so that the remote location 60 always has a current status.

It is also conceivable for several people to be in the work area at the same time in order to carry out work on current-carrying parts. In such situations, however, it can happen that an electrical accident involving a person 8 is not noticed by other persons in the vicinity, not even those in the immediate vicinity. This can also put other people at risk, for example, because they touch the person 8 who has become part of the electric circuit or because they also touch the live part. Apart from this, an efficient action to rescue the person 8 having the accident or to protect other people in the vicinity, for example by switching off or short-circuiting the electrical circuit or also by pushing the person 8 having the accident away, is only possible if at least one further person in the vicinity becomes aware of the electrical accident. In such cases, a protective device 1 according to the invention can also advantageously be used, as described by way of example with reference to FIG. 7.

Figure 8:
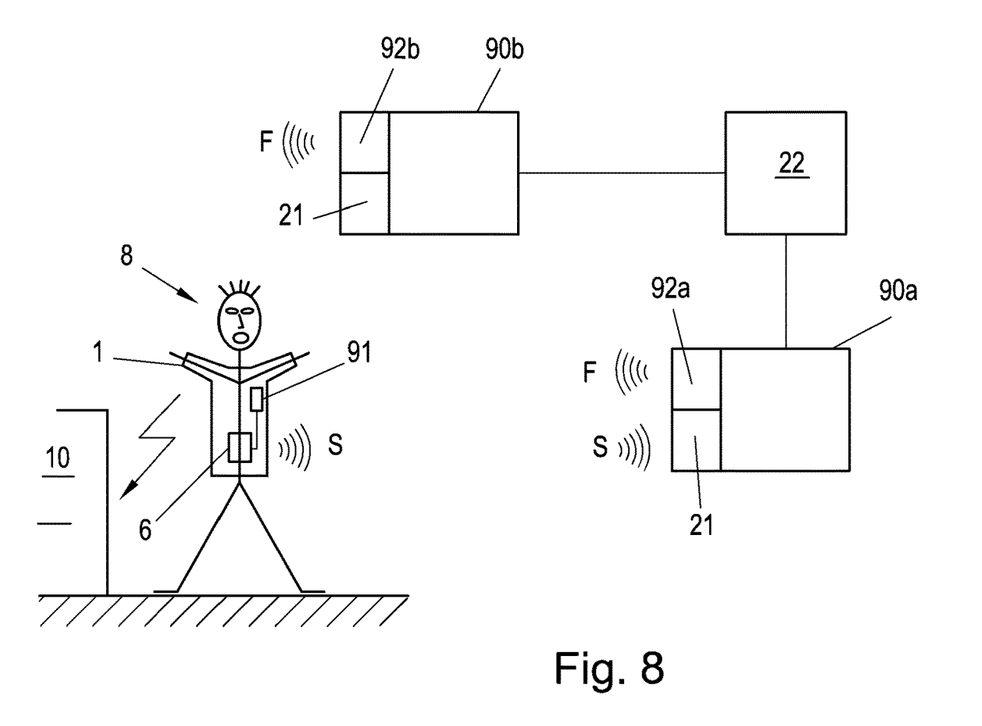

It is assumed that a plurality of people 8a, 8b, each with a protective device 1a, 1b, are in the vicinity of a live component and that the protective devices 1a, 1b are in communication. For this purpose, each protective device 1a, 1b can be provided with a communication unit 80a, 80b in order to be able to set up a communication link 81, for example via Bluetooth. The communication link 81 can, however, also be established indirectly, for example, as explained in connection with FIG. 5, via a mobile terminal 66 of a person 8a, 8b. The communication units 80a, 80b of the two protective devices 1a, 1b do not have to communicate directly with one another. It would be conceivable, for example, for a communication center 82 to be set up in the work area with which the individual protective devices 1a, 1b are connected via their communication units 80a, 80b, as indicated in FIG. 8. In that case, the communication link 81 is established via the communication center 82. The communication link 81 can be set up permanently or set up also on an event-related basis. If a protective device 1a of a person 8a triggers an emergency signal S, because this person 8a becomes part of an electric circuit, the communication unit 80a of the protective device 1a informs the at least one further person 8b in the vicinity via the communication link 81 and the communication unit 80b of the protective device 1b. For this purpose, a corresponding signaling unit, for example an acoustic, visual or palpable alarm, can also be provided on a protective device 1. If a protective device 1 is additionally provided with a unique identifier, it is possible to also transmit which protective device 1 is affected in order to be able to locate the person 8a having the accident more easily. The help for an person 8a having the accident can thus be considerably accelerated.

Instead of setting up a communication center 82 in the work area, the communication described could also take place via a remote location 60 (at any distance away) as a communication center, for example as described in FIG. 4 or 5.

The protective device 1 of the person 8 having the accident, or a communication unit 80 of the protective device 1 or an external device 71 coupled to the protective device, for example a mobile phone that the person 8 is carrying, can also make further persons in the surrounding area, who may not be trained or have any special equipment, aware of the danger and the help that is needed with a loud acoustic signal, optionally also with spoken warning text. An acoustic warning such as "Warning—electrical accident—this person is under voltage. Do not touch this person. Interrupt the circuit or remove the person from the circuit" or "Warning—electrical accident—this person has suffered an electric shock. Touchable parts under voltage are nearby" would be conceivable, for example.

In the case of a radio link for transmitting the output signal S from the protective device 1 to a radio receiver 90 of the electrical system 10, it is, of course, possible to check, either continuously or at least at the beginning of the work, whether a radio link exists at all. If not, a corresponding alarm can be issued by the protective device 1, for example acoustically, visually or palpably. The same naturally applies if a low state of charge of an energy supply for the protective device 1 is detected in the protective device 1.

In certain applications, for example in buildings, the radio link between the protective device 1 and the radio receiver for receiving the emergency signal can be interrupted easily and without noticing, in particular when the person 8 wearing the protective device 1 is moving. This can lead to false activations if a missing radio signal in the radio receiver triggers a switching action. In the worst case, the protective device 1 no longer provides protection for the person 8 carrying said device with this circumstance going unnoticed.

The electrical system 10 could also be configured differently depending on how dangerous the application is so that an interruption of the radio link forces a switch-off if the application is very dangerous but does not do so if the application is less dangerous.

Apart from that it may be provided according to the invention that at least two radio receivers 90a, 90b, each of which being provided with an emergency signal input 21 for receiving an emergency signal from the protective device 1, are spatially distributed in the working area of the person 8, as shown in FIG. 8. As described above, a radio receiver 90*a*, 90*b* can be connected to the safety module 22 of the electrical system 10 in order to detect an emergency signal S from the protective device 1 and to trigger a switching action. In this case, the emergency signal input 21 would be arranged externally from the electrical system 10.

The protective device 1 may be in bidirectional radio communication with the radio receivers 90*a*, 90*b*. This means that a signal receiver 91 is provided on the protective device 1 in order to be able to receive a radio signal F which is transmitted by a transmitter 92*a*, 92*b* in the radio receiver 90*a*, 90*b*. The signal receiver 91 is preferably arranged on the item of clothing 2 or integrated into the item of clothing 2 and connected to the evaluation unit 6 or another computing unit in the protective device 1. The radio signal F from a radio receiver 90*a*, 90*b* is sent continuously or at least at regular intervals and is received by the signal receiver 91 of the protective device 1. The protective device 1 is thus able to evaluate the signal quality of the radio channel between the protective device 1 and a radio receiver 90*a*, 90*b*. The protective device 1 can thus decide over which of the available radio channels the emergency signal S is to be sent.

A plurality of such radio receivers 90*a*, 90*b* can be distributed in a building or a system, and the protective device 1 can select a radio receiver 90*a*, 90*b*, for example the radio channel with the best signal quality, in order to transmit the emergency signal S via said channel. This way, the person 8 who wears the protective device 1 can move through the building or the installation without losing the radio link.

For the invention, however, it is in principle unimportant where the decision which radio receiver 90*a*, 90*b* is used for communication purposes is made. The decision could be made in the signal receiver 91, in the radio receivers 90*a*, 90*b*, in the safety module 22 or elsewhere.

The invention claimed is:

1. Arrangement for carrying out work on an electrical installation by a person, wherein the electrical system comprises:
   a plurality of electrical circuits each with a switch configured and arranged for switching off the associated circuit of the plurality of electrical circuits,
   a safety module including an emergency signal input, and the safety module is configured and arranged to
      switch off a first circuit of the plurality of electrical circuits via the associated switch when an external emergency signal is received via the emergency signal input and
      at least one further circuit of the plurality of electrical circuits is switched off via an associated switch, when the safety module continues to receive the emergency signal at the emergency signal input after a predetermined period of time; and
   a protective device configured and arranged to be worn by the person and for detecting an electrical body current which, in the event that an unacceptable body current is detected, generates the emergency signal and transmits said signal to the emergency signal input of the safety module.

2. The arrangement according to claim 1, characterized in that a hierarchy of the plurality of electrical circuits is configured in the safety module according to which the safety module switches off the circuits.

3. The arrangement according to claim 1, characterized in that a plurality of circuits can be switched off at the same time in a hierarchical level.

4. The arrangement according to claim 1, characterized in that the protective device includes
   an item of clothing configured and arranged to be worn by the person and
   an evaluation unit,
   wherein the item of clothing includes at least one sensor configured and arranged for detecting the body current, and
   wherein the evaluation unit is configured and arranged to evaluate a signal detected by the at least one sensor and emits the emergency signal in the event of a detected unacceptable body current.

5. The arrangement according to claim 4, characterized in that the protective device includes at least one further sensor that detects a further state of the person wearing the protective device and/or a unit for determining the position or location of the person.

6. The arrangement according to claim 1, further including a remote location configured and arranged to receive a signal from the protective device in the event of an electrical accident.

7. The arrangement according to claim 6, characterized in that the protective device of the remote location is also configured and arranged to transmit data from the at least one further sensor and/or the position or location of the person.

8. The arrangement according to claim 6, characterized in that the remote location is further configured and arranged to coordinate assistance for the person after an electrical accident.

9. The arrangement according to claim 1, characterized in that at least one further person, who is also wearing a protective device, is in the area where the person is working, wherein the protective device of the person and the protective device of the at least one further person have a communication link, wherein the protective device of the person informs the protective device of the at least one further person about an electrical accident of the person via the communication link.

10. The arrangement according to claim 9, characterized in that the protective devices each include a communication unit configured and arranged for establishing the communication link.

11. The arrangement according to claim 10, further including a communication center that is configured and arranged to be communicatively connected to the communication units in order to establish the communication link.

12. The arrangement, according to claim 1, characterized in that the protective device is further configured and arranged to output an acoustic warning and/or an acoustic warning text in the event of an electrical accident.

13. The arrangement according to claim 1, characterized in that the protective device is configured and arranged to
   transmit the emergency signal by radio to the emergency signal input, and
   output an alarm in the event that there is no radio connection with the safety module.

14. The arrangement according to claim 1, characterized in that the safety module is connected to a plurality of radio receivers, each of the plurality of radio receivers having an emergency signal input,
   wherein the protective device includes a signal receiver configured and arranged to receive a radio signal transmitted by the at least one of the plurality of radio receivers, and evaluate the signal quality of a radio channel between the protective device and a radio receiver via the received radio signal, and selecting the radio channel with the best signal quality for sending an emergency signal.

15. Method for carrying out work on an electrical installation by a person, wherein the electrical installation is provided with a plurality of electrical circuits each with a switch for switching off the associated circuit of the plurality of electrical circuits, the method including the following steps:

detecting an electrical body current via a protective device worn by the person, in the event that an unacceptable body current is detected, outputting an emergency signal and transmitting said signal to an emergency signal input of a safety module, receiving, at the emergency signal input of the safety module, the external emergency signal, in response to the external emergency signal, switching off a first circuit via an associated switch, and switching off at least one further circuit of the plurality of electrical circuits via the associated switch when the safety module still receives the emergency signal at the emergency signal input after a predetermined period of time.

16. The method according to claim 15, characterized in that a hierarchy of the plurality of electrical circuits is configured in the safety module according to which the safety module switches off the first and at least one further circuits.

17. The method according to claim 16, characterized in that the plurality of circuits in a hierarchy level can be switched off at the same time.

18. The method according to claim 15, further including the step of the protective device informing a remote location in the event of an electrical accident.

19. The method according to claim 18, further including the step of the protective device transmitting to the remote location data from at least one further sensor on the protective device and/or the position or location of the person.

20. The method according to claim 18, further including the step of coordinating help for the person after an electrical accident by the remote location.

21. The method according to claim 15, characterized in that at least one further person also wearing another protective device is in the area where the person is working, the method further including the steps of establishing a communication link between the protective device of the person and the other protective device of the at least one further person, informing the protective device of the at least one further person via the communication link about an electrical accident of the person.

22. The method according to claim 18, further including the step of outputting an acoustic warning and/or an acoustic warning text from the protective device in the event of an electrical accident.

23. The method according to claim 18, further including the step of transmitting the emergency signal from the protective device by radio to the emergency signal input and outputting an alarm in the event that there is no radio connection.

24. The method according to claim 18, characterized in that the safety module is connected to a plurality of radio receivers each having an emergency signal input, wherein the protective device includes a signal receiver that receives a radio signal transmitted by the radio receiver, and the signal quality of a radio channel between the protective device and a radio receiver is evaluated via the radio signal, and the radio channel with the best signal quality for sending the emergency signal is selected.

* * * * *